US00PP27170P2

(12) United States Plant Patent
Jansen

(10) Patent No.: US PP27,170 P2
(45) Date of Patent: Sep. 20, 2016

(54) ***GAULTHERIA* PLANT NAMED 'SPECGP11'**

(50) Latin Name: *Gaultheria procumbens*
Varietal Denomination: SPECGP11

(71) Applicant: Johan Jansen, Zundert (NL)

(72) Inventor: Johan Jansen, Zundert (NL)

( * ) Notice: Subject to any disclaimer, the term of this patent is extended or adjusted under 35 U.S.C. 154(b) by 115 days.

(21) Appl. No.: 14/544,330

(22) Filed: Dec. 23, 2014

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Gautheria procumbens* plant, 'SPECGP11', that is characterized by its white berries, its pure white flowers, and its burgundy fall foliage color.

2 Drawing Sheets

Botanical classification: *Gaultheria procumbens.*
Cultivar designation: 'SPECGP11'.

BACKGROUND OF THE INVENTION

The present invention relates to a new and distinct cultivar of *Gaultheria procumbens* named 'SPECGP11' and is hereinafter referred to by the cultivar name 'SPECGP11'. 'SPECGP11' represents a new cultivar of eastern teaberry or American wintergreen that is grown as a landscape plant.

The new cultivar arose as a seedling selected by the Inventor in Zundert, The Netherlands. The Inventor sowed seeds that he collected from unnamed and unpatented plants of *Gaultheria procumbens* that were growing in his garden. The Inventor selected 'SPECGP11' in January of 2008 as a single unique plant amongst the seedlings that resulted from the sowing.

Asexual propagation of the new cultivar was first accomplished by the Inventor by cuttings in Zundert, The Netherlands in 2009. Asexual propagation of the new cultivar by cuttings and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'SPECGP11' as a new and unique cultivar of *Gautheria.*

1. 'SPECGP11' exhibits white berries.
2. 'SPECGP11' exhibits pure white flowers.
3. 'SPECGP11' exhibits burgundy fall foliage color.

Typical plants of the parent species of 'SPECGP11', *Gaultheria procumbens*, differ primarily in having red fruit and there are no varieties or cultivars known to the Inventor that exhibit red fruit. The only cultivars of *Gaultheria procumbens* known to the Inventor, 'Red Baron' and 'Very Berry' (both not patented), exhibit red fruit. The only plants of *Gaultheria* known to the Inventor with white fruit are those of different species.

BRIEF DESCRIPTION OF THE DRAWINGS

The accompanying colored photographs illustrate the overall appearance and distinct characteristics of the new cultivar.

The photographs were taken of a plant about one year in age as grown in a 105-cm container in Zundert, The Netherlands.

Figure 1:
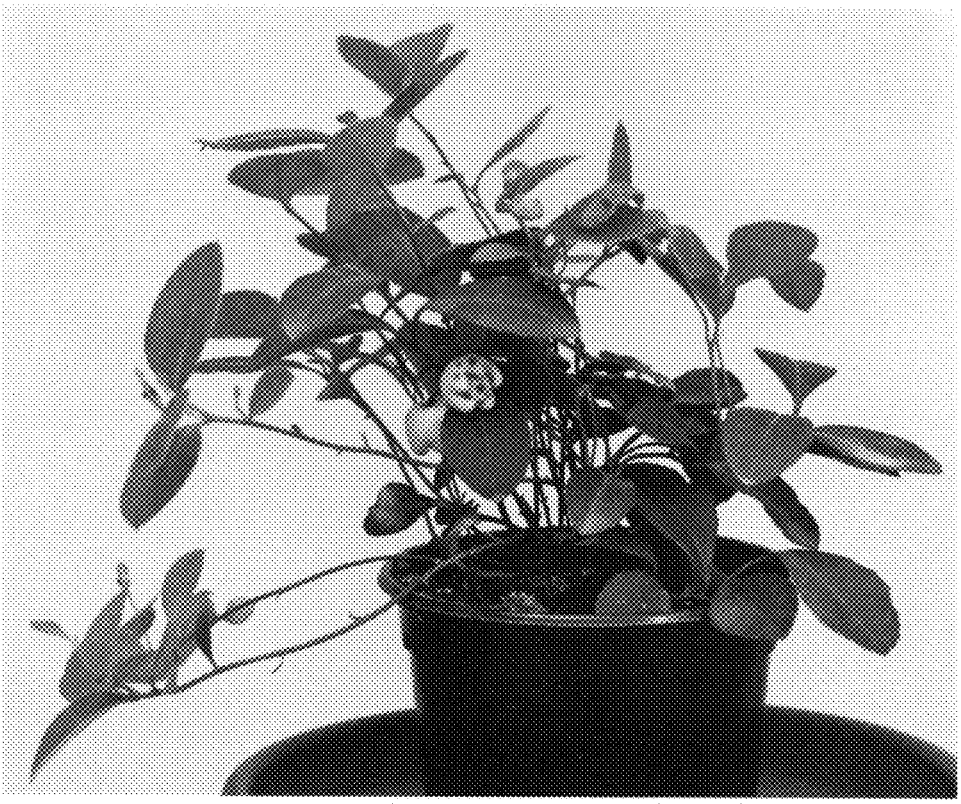

The photograph in FIG. 1 provides a side view of a plant of 'SPECGP11' in fruit.

Figure 2:
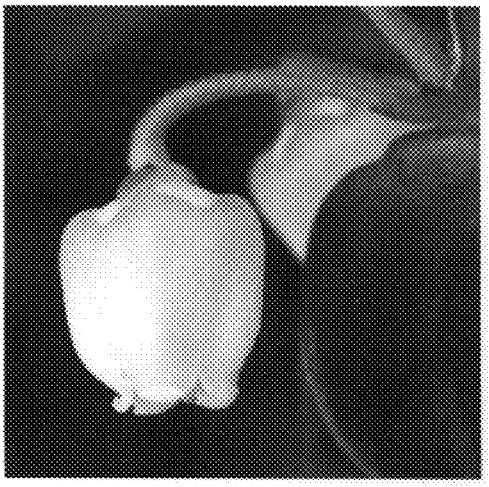

The photograph in FIG. 2 provides a close-up view of the flowers of 'SPECGP11'.

Figure 3:
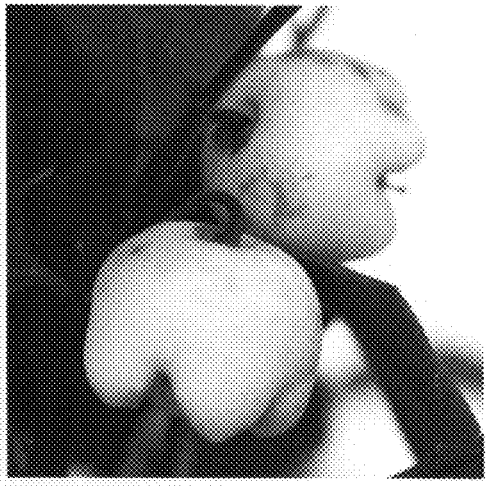

The photograph in FIG. 3 provides a close-up view of the fruit of 'SPECGP11'.

Figure 4:
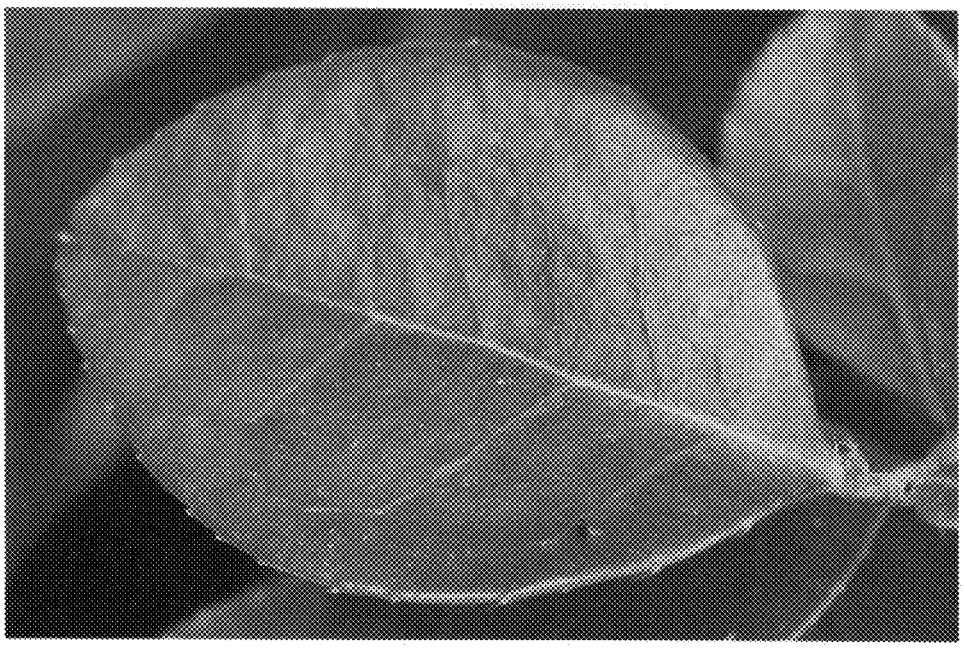

The photograph in FIG. 4 provides a close-up view of the summer foliage of 'SPECGP11'.

The colors in the photographs are as close as possible with digital photography techniques available and the color values cited in the detailed botanical description accurately describe the colors of the new cultivar of *Gautheria.*

DETAILED BOTANICAL DESCRIPTION OF THE PLANT

The following is a detailed description of plants about one year in age as grown in 10.5-cm containers in Zundert, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late spring to late summer (about 4 weeks) in The Netherlands.

*Plant type.*—Evergreen shrub.

*Plant habit.*—Broadly spreading, groundcover once established.

*Height and spread.*—15 cm in height and 20 cm in width as a one year-old plant in a 10.5-cm container.

*Cold hardiness.*—At least in U.S.D.A. Zone 4.

*Diseases and pests.*—No particular resistance or susceptibility to diseases or pests has been observed.

*Propagation.*—Tissue culture (preferred) and cuttings.

*Root development.*—A rooted liner will take about 3 months to develop in a 10.5 Liter container.

*Growth rate and vigor.*—Moderate.

Stem description:

*Shape*.—Ovate.

*Stem color*.—New and mature growth; 180A.

*Stem size*.—An average of 9.5 cm in length and 1.5 mm in width.

*Stem surface*.—Young stems moderately glossy and densely covered with very short hairs, mature stems moderately covered with very short hairs; both 0.5 mm in length an NN155D in color.

*Branching*.—Freely branched, an average of 17 basal branches.

*Branch angle*.—Upright to prostrate.

*Branch internode length*.—Average of 1 cm.

Foliage description:

*Leaf shape*.—Elliptic to obovate.

*Leaf division*.—Simple.

*Leaf base*.—Attenuate.

*Leaf apex*.—Broadly acute.

*Leaf fragrance*.—Wintergreen if crushed.

*Leaf venation*.—A nastomosing, upper surface; 152D in color and densely covered with short adpressed hairs an average of 0.75 mm in length and 156D to 156D in color.

*Leaf margins*.—Shallowly and irregularly serrate.

*Leaf arrangement*.—Alternate and clustered near tips.

*Leaf attachment*.—Petiolate.

*Leaf number*.—Average of 6 per branch.

*Leaf surface*.—Upper and lower surface; glabrous, slightly glossy, and leathery.

*Leaf size*.—Average of 4.7 cm in length and 2.6 cm in width, lower surface; primary veins 145B in color with base 182D.

*Leaf color*.—Young leaves upper surface; slightly darker than 143A, young leaves lower surface; 146B, mature leaves upper surface; a color between N137A and 147A but slightly darker, mature leaves lower surface; a color between 156C and 156D, fall color upper and lower surface; 187A.

*Petioles*.—Average of 5 mm in length and 1.5 mm in width, upper surface 178A in color, lower surface 180A in color, surface is glabrous and slightly glossy.

*Stipules*.—None observed.

Inflorescence description:

*Inflorescence*.—Axillary and terminal panicles.

*Inflorescence size*.—Average of 3.9 cm in length and 3.2 cm in width.

*Lastingness of inflorescence*.—Average of 2 weeks, self cleaning.

*Number of flowers*.—Average of 9 per inflorescence, range of 4 to 13, average of 150 per plant.

*Flower fragrance*.—None.

*Rate of opening*.—20% open at first and all remain open as the rest open.

*Flower buds*.—Ovate in shape, average of 5 mm in length and 3 mm in width, 150D in color.

*Flower size*.—Average of 9 mm in length and 8 mm in width.

*Corolla*.—Urceolate in shape, comprised of 5 fused ovate shaped petals with rounded tips (10%) free that are curled under and 2 mm in width, color NN155C to NN155D on both surfaces when opening and mature, surface glabrous and matte and very slightly ribbed on inner and outer surfaces.

*Calyx*.—Rotate in arrangement, average of 2.5 mm in length and 5 mm in diameter.

*Sepals*.—5, average of about 3 mm in length and 2 mm in width, color when young 157D on upper and lower surface, color when mature NN155B on upper and inner surface.

*Peduncles*.—Round, terminal held upright to stem with axillary peduncle an average of 40° angle to stem, an average of 4.4 cm in length and 1 mm in width, 145B in color, pubescent surface.

*Pedicels*.—Round, average of 1.4 cm in length and 8 mm in width, held at an angle of 45° to peduncle, 145A to 145B in color with upper surface tinged with 180A to 180B, pubescent surface.

Reproductive organs:

*Androecium*.—Average of 10 stamens, anthers are dorsifixed, narrow deltoid in shape, 200A to 200B in color and 2 mm in length, filaments are 3 mm in length and NN155C in color, pollen is very low in quantity and 164D in color.

*Gynoecium*.—1 pistil, stigma is narrow club-shaped with an obtuse apex, 6 mm in length, and 157D in color, style is an average of 6 mm in length and 157D in color, ovary is 145B in color.

Fruit description:

*Type*.—Berry.

*Number*.—1 to 2 per lateral branch.

*Fruit size*.—Average of 1.2 cm (excluding persistent style; 1.5 cm inclusive) and 1.5 cm in width NN155B and very slightly tinged in areas with 159B to 159C.

*Fruit surface*.—Matte.

*Fruit shape*.—Rounded with indented apex and 5 extended tips.

*Seeds*.—Numerous dust-like seeds, less than 0.3 m in length and width, 199B to 199D in color.

It is claimed:

1. A new and distinct cultivar of *Gaultheria* plant named 'SPECGP11' as herein illustrated and described.

* * * * *